(12) United States Patent
Delulio (10) Patent No.: US 9,855,406 B2
(45) Date of Patent: Jan. 2, 2018

(54) UMBILICAL LINE-SECURING DEVICE AND METHOD

(71) Applicant: David Delulio, Lafayette, LA (US)

(72) Inventor: David Delulio, Lafayette, LA (US)

( * ) Notice: Subject to any disclaimer, the term of this patent is extended or adjusted under 35 U.S.C. 154(b) by 614 days.

(21) Appl. No.: 14/181,700

(22) Filed: Feb. 16, 2014

(65) Prior Publication Data

US 2016/0339209 A1 Nov. 24, 2016

Related U.S. Application Data

(60) Provisional application No. 61/765,717, filed on Feb. 16, 2013.

(51) Int. Cl.
*A61M 25/02* (2006.01)

(52) U.S. Cl.
CPC ....... *A61M 25/02* (2013.01); *A61M 2025/028* (2013.01); *A61M 2025/0213* (2013.01); *A61M 2205/02* (2013.01); *A61M 2210/12* (2013.01); *A61M 2240/00* (2013.01)

(58) Field of Classification Search
CPC .......... A61M 25/02; A61M 2025/0206; A61M 2025/024; A61M 2025/026; A61M 2025/0286; A61M 2025/028; A61M 2025/0213; A61M 2005/1586; A61B 17/122; A61B 5/6823; A61B 5/3831; A61B 90/30; F16L 3/2235; F16L 3/233; Y10S 128/26

See application file for complete search history.

(56) References Cited

U.S. PATENT DOCUMENTS

| | | | | |
|---|---|---|---|---|
| 4,659,329 A | * | 4/1987 | Annis | A61M 25/02 128/DIG. 26 |
| 5,795,335 A | * | 8/1998 | Zinreich | A61M 25/02 128/DIG. 26 |
| 6,231,547 B1 | * | 5/2001 | O'Hara | A61M 25/02 604/174 |
| 2011/0282290 A1 | * | 11/2011 | Kennard | A61M 25/02 604/174 |
| 2012/0232358 A1 | * | 9/2012 | Coelho | A61B 5/0205 600/301 |
| 2014/0061421 A1 | * | 3/2014 | Lane | F16L 3/221 248/542 |

* cited by examiner

*Primary Examiner* — Matthew F Desanto (57) ABSTRACT

An umbilical line-securing device adapted to nonadhesively maintain an umbilical line at a location relative to an umbilical stump.

20 Claims, 7 Drawing Sheets

UMBILICAL LINE-SECURING DEVICE AND METHOD

This Application claims priority to and benefit of U.S. Provisional Patent Application No. 61/765,717, which was filed on Feb. 16, 2013, and is incorporated herein by reference in its entirety.

FIELD OF THE DISCLOSURE

The present disclosure relates to medical devices, and more particularly, to a device for securing umbilical lines to a baby.

RELATED ART

The skin of a baby is typically underdeveloped and may not be suitable as an anchor for traditional medical devices. A premature or sick full term baby may require the repeated delivery of medicine and/or fluid during the first several days and/or weeks of life. Central lines allow for the delivery of these fluids or medications, allow for the accurate continuous monitoring of vital signs, and are convenient for blood sampling.

Rather than repeatedly inserting needles into the skin, one or more intravenous lines can be inserted into, and maintained within, an umbilical stump of the baby. The umbilical stump typically contains one umbilical vein and two smaller umbilical arteries. The intravenous lines, also known as umbilical lines, are inserted into the umbilical vein and arteries using a process known as cannulation. The umbilical lines offer a way of delivering medicines and fluids, and performing tests and monitoring vital signs, all while simultaneously avoiding repeated needle insertions.

Proper placement of the umbilical lines within the baby is vital to the proper delivery of fluids. Incorrect placement can result in potentially fatal complications. Similarly, any movement, or translation, of the umbilical line(s) within the umbilical vein and arteries in the days and weeks following cannulation can cause, or magnify, complications and can lead to fatality.

Traditional devices and methods for securing the umbilical lines involve the use of adhesives disposed between the securing device and the skin of the baby. Because of the fragile condition of baby's skin following birth, these adhesives can be irritating, damaging, and can reduce the chance of survival. Moreover, these devices are frequently difficult and very time consuming to set up and adjust, and may need to be replaced.

The industry continues to demand improvements in umbilical line-securing devices and techniques.

BRIEF DESCRIPTION OF THE DRAWINGS

Embodiments are illustrated by way of example and are not limited in the accompanying figures.

DETAILED DESCRIPTION

The following description in combination with the figures is provided to assist in understanding the teachings disclosed herein. The following discussion will focus on specific implementations and embodiments of the teachings. This focus is provided to assist in describing the teachings and should not be interpreted as a limitation on the scope or applicability of the teachings. However, other embodiments can be used based on the teachings as disclosed in this application.

The terms "comprises," "comprising," "includes," "including," "has," "having" or any other variation thereof, are intended to cover a non-exclusive inclusion. For example, a method, article, or apparatus that comprises a list of features is not necessarily limited only to those features but may include other features not expressly listed or inherent to such method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

Also, the use of "a" or "an" is employed to describe elements and components described herein. This is done merely for convenience and to give a general sense of the scope of the invention. This description should be read to include one, at least one, or the singular as also including the plural, or vice versa, unless it is clear that it is meant otherwise. For example, when a single item is described herein, more than one item may be used in place of a single item. Similarly, where more than one item is described herein, a single item may be substituted for that more than one item.

Unless otherwise defined, all other technical and scientific terms used herein have the same meaning as commonly understood by one of ordinary skill in the art to which this invention belongs. The materials, methods, and examples are illustrative only and not intended to be limiting. To the extent not described herein, many details regarding specific materials and processing acts are conventional and may be found in textbooks and other sources within the medical device arts.

An umbilical line-securing device can generally include a receiving member adapted to receive at least one umbilical line. The receiving member can be adapted to be disposed at a location proximate to an umbilical stump of a neonate. In such a manner, the umbilical line-securing device can secure the umbilical line and reduce, or prevent, movement of the umbilical line relative to an umbilical stump of the neonate.

Referring initially to FIGS. 1 to 4, in a first aspect, an umbilical line-securing device 1 can generally include a receiving member 2 adapted to receive at least one umbilical line 100/102. In a preferred embodiment, the umbilical line-securing device 1 can receive a first umbilical line 100 and a second umbilical line 102. The umbilical line-securing device 1 can secure the umbilical lines 100 and 102 to an umbilical stump 104 of a baby 106. In such a manner, the umbilical line-securing device 1 can mitigate longitudinal and transverse movement of the umbilical lines 100 and 102 within the umbilical stump 104 and can reduce complications that may arise as the result of unsecured umbilical lines, such as, for example, damage to the vein or artery, exsanguination, infection, organ damage from improper umbilical line placement, etc.

In particular embodiments, the umbilical line-securing device 1 can further include a securing member 4 connected to the receiving member 2. The securing member 4 can be adapted to secure the receiving member 2 to the umbilical stump 104 of the neonate 106. In this regard, the umbilical line-securing device 1 can secure the at least one umbilical line 100 to the baby 106 at a location adjacent to the umbilical stump 104.

Figures 1, 2:
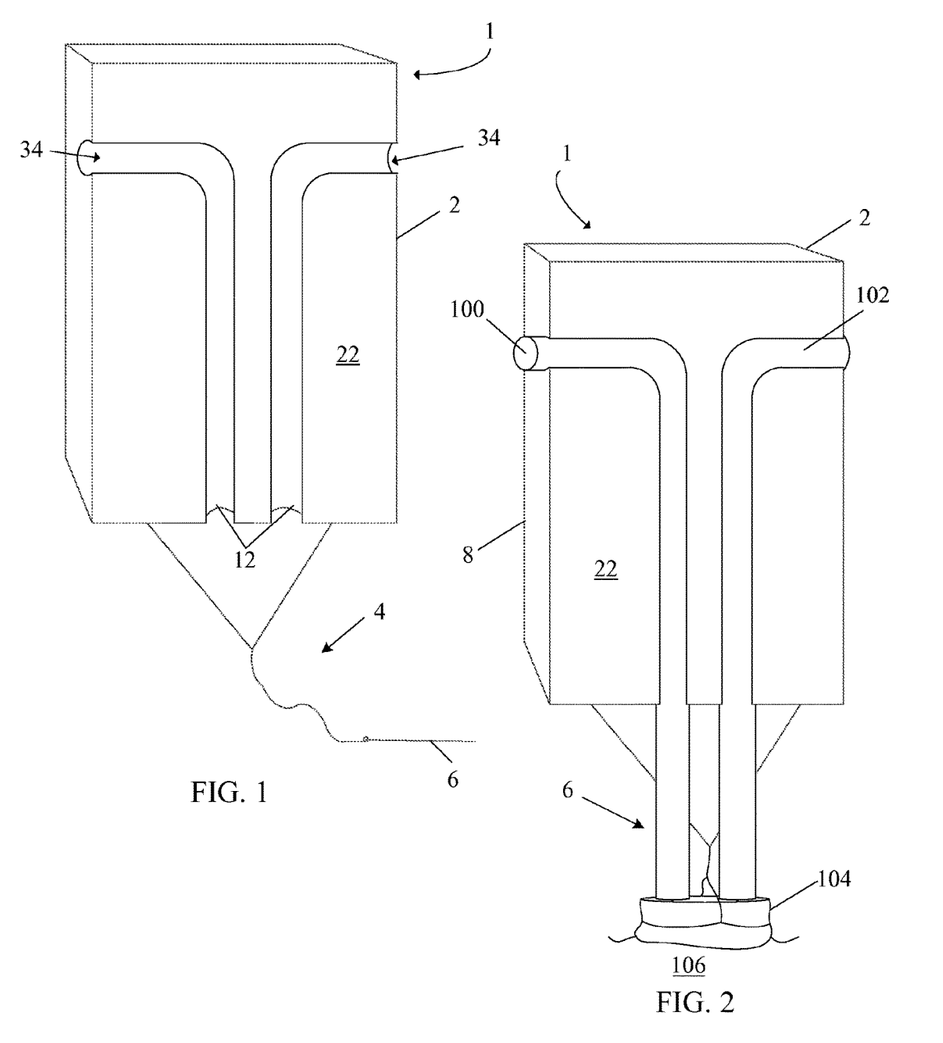
FIG. 1 includes a perspective view of an umbilical securing device in accordance with an embodiment.
FIG. 2 includes a perspective view of an umbilical securing device securing umbilical lines to an umbilical stump in accordance with an embodiment.
Figure 3:
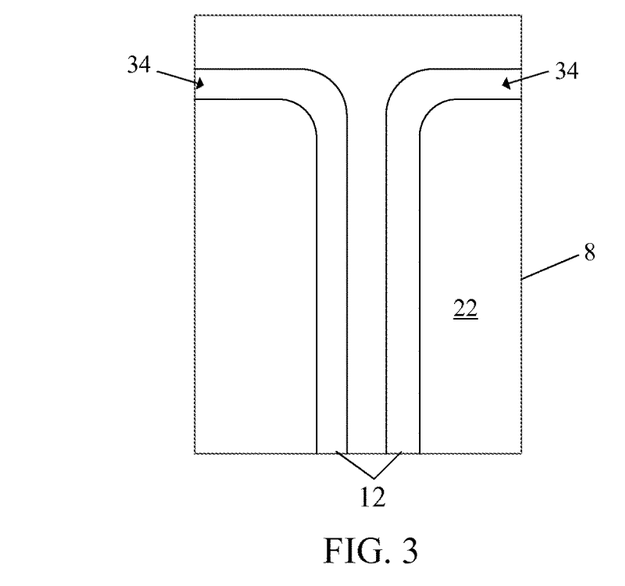
FIG. 3 includes a front view of a receiving member in accordance with an embodiment.

Referring specifically to FIG. 1, the securing member 4 can include a thread, such as a suture with a piercing device, e.g., a needle 6. In such a manner, the piercing device can penetrate the umbilical stump 104 and can allow the suture to be secured to the umbilical stump 104. In another embodiment, the securing member 4 can include a suture without a piercing device. In this regard, the suture can be tied around the umbilical stump 104 without piercing therethrough. In a further embodiment, the piercing device can be passed through the umbilical stump 104 and a knot can be formed around the umbilical stump 104 (FIG. 2). In particular embodiments, it may be beneficial to have the securing member 4 short after attachment with the umbilical stump 104 such that a minimal gap (e.g., less than 1 inch, less than 0.5 inches, or even less than 0.2 inches) exists between the umbilical stump 104 and the receiving member 2. However, it may be advantageous for the securing member 4 to have a greater length prior to attachment, to allow for easier operation and handling.

A person of ordinary skill will understand that the embodiments herein are not intended to be limited by the scope of the securing member 4. For example, as contemplated herein, the securing member 4 can include a hook-and-loop engagement (e.g., Velcro®), a twisting element (e.g., a line having a twistable function that can be twisted around the umbilical stump such as a twist tie), a band adapted to fit around the umbilical stump (e.g., an elastic band, a locking annular band, a ratchet band, or a zip tie), or any combination thereof. The securing member 4 can comprise a rigid construction or a flexible construction. Moreover, the securing member 4 can comprise one component, e.g., a suture, or multiple components attached together, e.g., a zip tie attached to a suture. As will be discussed in greater detail below, in particular embodiments, the umbilical line-securing device 1 can comprise an attachment device, such as a ring, e.g., a D-shaped ring, to allow a suture, or other securing device, to be attached to the receiving member 2 after manufacture.

In particular embodiments, the umbilical line-securing device 1 can be devoid of an adhesive, such that the umbilical line-securing device 1 is a nonadhesive umbilical line-securing device. In other embodiments, the securing member 4 can be adhesiveless, i.e., it does not include an adhesive, while the receiving member 2 can include an adhesive material, e.g., a tacky adhesive for grip and support of an umbilical line. As used herein, the terms "nonadhesive," "adhesiveless," or any derivations thereof, refer to a nonadhesive engagement of the umbilical line-securing device with the umbilical stump or with the umbilical lines. Accordingly, adhesive can be used in parts of the umbilical line-securing device, such as, for example, attaching components of the receiving member together. In particular embodiments, the terms "nonadhesive" and "adhesiveless" can indicate a nominal amount of adhesiveness, e.g., a tackiness adapted to enhance gripping characteristics between two objects while simultaneously permitting easy detachment therebetween, or a tackiness to increase relative friction between two objects. However, a person of ordinary skill will understand that "nonadhesive" and "adhesiveless" indicate a securement not made primarily by the adhesion properties of an adhesive.

The receiving member 2 can generally comprise a body 8 having a polygonal shape, a rounded shape, or a combination thereof. For example, referring to FIG. 5, in particular embodiments the body 8 can have a T-shape, or a Y-shape. In this regard, the body 8 can be shaped to receive the umbilical lines 100 and can have a non-rectangular shape for easier handling. At least some of the corners and edge surfaces of the body 8 can be right angled, beveled, rounded, or contain any combination thereof. This may reduce the likelihood that the receiving member scratches the baby upon contact.

The body can further have any number of design features, including, for example, a fillet, a bevel, a hole, a projection, a tab, a protrusion, indicia, a rounded corner, a concave portion, a convex portion, or any combination thereof. It should be understood that the shape of the body is not intended to be limited by the disclosure herein, and can instead take many forms.

In particular embodiments, the body can have a monolithic construction, i.e., it can be formed from a single piece of material. In other embodiments, such as illustrated in FIG. 7, the body 8 can comprise a multi-piece construction, i.e., it is not monolithic.

A body 8 having a multi-piece construction can be assembled by any method recognizable to a person having ordinary skill in the art, such as, for example, by an adhesive, a threaded or non-threaded fasteners, an outer coating (as will be discussed in greater detail below), or any combination thereof.

A multi-piece body 8 can have at least two components, such as at least three components, at least four components, at least five components, at least six components, at least seven components, at least eight components, at least nine components, or even at least ten components. In a first aspect, the components of the body 8 can be statically coupled together. In a second aspect, the components of the body 8 can be dynamically coupled. More particularly, at least two of the components of the body 8 can be coupled via one or more hinges 14 (FIG. 7).

Figure 7:
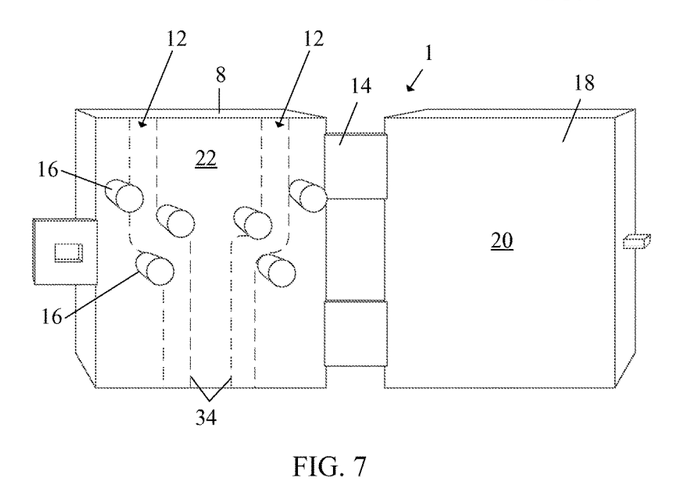
FIG. 7 includes a perspective view of a receiving member in accordance with an embodiment.

As illustrated in FIG. 7, the body 8 can include one or more posts 16 extending from a first surface 22 of the body 8. The posts 16 can define one or more passageways 12 each adapted to support one umbilical line. The posts 16 can be spaced apart to allow insertion of the umbilical lines into the passageways 12. The posts 16 can be cylindrical, frusto-conical, dome-shaped, or any combination thereof. Moreover, the posts can comprise any one of a serration, a bend, a flexible portion, a notch or channel to receive or secure the umbilical lines, or any combination thereof. The posts 16 can be hollow or have a uniform cross sectional composition. The posts 16 can extend in a direction normal to a surface of the body 8 or at a relative angle. In a first embodiment, the posts 16 can have the same or similar material as the body 8. In a second embodiment, the posts 16 can be formed from a different material than the body 8. The posts 16 can be secured to the body 8 by an adhesive, a threaded or non-threaded fastener, or by any other method recognizable in the art. Alternatively, the posts 16 can be formed together with the body 8, i.e., the posts 16 and the body 8 are monolithic.

A second component 18 of the umbilical line-securing device 1 can have an inner surface 20 adapted to receive the posts 16, i.e., the posts 16 compress into the inner surface 9. Alternatively, the hinge 14 can be adapted such that an axial end of each post 16 touches, or nearly touches, the inner surface 20 of the second component 18 when the umbilical securing device 1 is closed (not shown). The umbilical lines (not shown) can be inserted between the posts 16 along passageways 12 and can be retained between surfaces 20 and 22 when the umbilical line-securing device 1 is in the closed orientation.

In particular embodiments, the body 8 can comprise a material having a density of at least 0.01 g/cm$^3$, such as at least 0.1 g/cm$^3$, at least 0.2 g/cm$^3$, at least 0.5 g/cm$^3$, or even at least 1.0 g/cm$^3$. In other embodiments, the body 8 can comprise a material having a density of less than 100 g/cm$^3$, such as less than 50 g/cm$^3$, less than 25 g/cm$^3$, less than 10 g/cm$^3$, or even less than 5 g/cm$^3$.

In a further embodiment, the body 8 can have a total mass of less than 500 grams, such as less than 250 grams, less than 100 grams, less than 75 grams, less than 50 grams, less than 25 grams, or even less than 10 grams. In this regard, the body 8 can be lightweight and easy to maneuver. It should be understood that the body 8 can have a mass of at least 1 gram. Moreover, the body 8 can have a mass within a range between and including any of the values described above, such as, for example, between 15 grams and 30 grams.

In particular embodiments, the body 8 can be constructed at least partially from a polymer. In other embodiments, the body 8 can be constructed at least partially from a metal. Moreover, the body 8 can comprise any other material, such as, for example, a ceramic or an alloy. In certain embodiments, the body 8 can have a combination of metal and polymer. The body 8 can be formed, for example, by molding, injection molding, extruding, casting, rolling, shaping, or any combination thereof.

In a non-limiting embodiment, the securing member 4 can be attached directly to the body 8 of the receiving member 2. For example, the body 8 can optionally include a loop or ring (not shown) disposed at a location along an outer surface. The securing member 4 can engage with the loop or ring via a knot, an adhesive, or any other attachment method recognizable in the art. In this regard, the securing member 4 can be provided as a separate feature and attached to the receiving member 2 after manufacture. In a further example, the securing member 4 can be attached to the body 8 by an outer coating 10 (FIG. 4).

Figure 4:
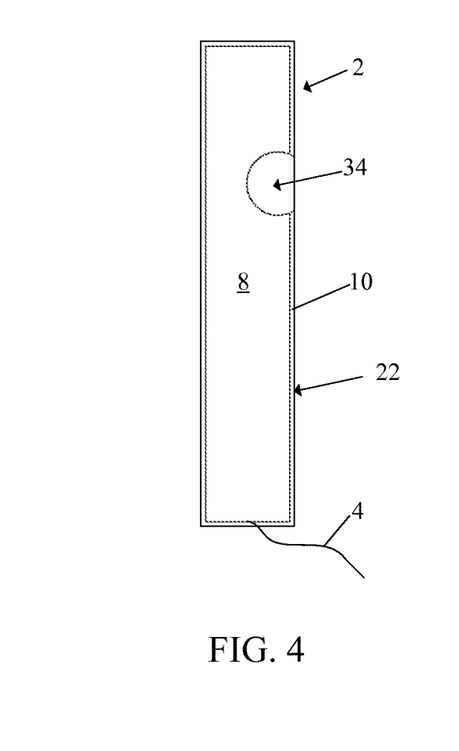
FIG. 4 includes a side view of a receiving member in accordance with an embodiment.

Referring to FIG. 4, in particular embodiments, the receiving member 2 can further include an outer coating 10 disposed around the outer surface of the body 8. A portion of the securing member 4 can be disposed between the outer surface of the body 8 and the outer coating 10. Alternatively, a portion of the securing member 4 can be disposed within the outer coating 10 to an extent sufficient to hold the securing member 4 thereto, and prevent the securing member 4 from disengaging from the body 8. Alternatively, the securing member 4 can be attached directly to the body 8 and the coating can further assist in securing the securing member 4 thereto.

In particular embodiments, the outer coating 10 can generally comprise a polymer. In particular, the outer coating 10 can at least partially comprise an elastomer. More particularly, the outer coating 10 can at least partially comprise a thermoplastic elastomer (TPE). Exemplary elastomers can include a rubber, a polyisoprene, a polybutadiene, a chloroprene rubber, a polychloroprene, a silicone, vinylidene fluoride and hexafluoropropylene, a santoprene, a flurorsilicone rubber, a ethylene propylene rubber, a prolyurethane rubber, a resilin, a polyacrylic rubber, a epichlorohydrin rubber, a polysulfide rubber, a chlorsulfonated polyethylene, a polyether block amide, or any combination thereof. Other polymers can include a polyketone, a polyaramid, a polyimide, a polyetherimide, a polyamideimide, a polyphenylene sulfide, a polyphenylene sulfone, a fluoropolymer, a polybenzimidazole, a derivation thereof, or a combination thereof. In a particular example, the outer coating 10 can include a polymer, such as a polyketone, a thermoplastic polyimide, a polyetherimide, a polyphenylene sulfide, a polyether sulfone, a polysulfone, a polyamideimide, a derivative thereof, or a combination thereof. In a further example, the material includes polyketone, such as polyether ether ketone (PEEK), polyether ketone, polyether ketone ketone, polyether ketone ether ketone, a derivative thereof, or a combination thereof. It should be understood that the described polymers herein are solely exemplary, and are not intended to be limited by the aforementioned polymers and that a wide range of materials are suitable.

In further embodiments, the outer coating 10 can have a thickness, as measured in a direction normal to a surface of the body 8, of between 0.005 inches and 0.50 inches. In more particular embodiments, the outer coating 10 can have a thickness of between 0.05 inches and 0.25 inches. In yet more particular embodiments, the outer coating 10 can have a thickness of between 0.05 inches and 0.15 inches. Moreover, the outer coating 10 can have a thickness within a range between and including any of the values described above, such as, for example, between 0.15 inches and 0.25 inches.

In particular embodiments, the outer coating 10 can comprise a material having a dry coefficient of static friction, as measured against the umbilical line 100 at room temperature, that is greater than at least 0.01, such as greater than at least 0.05, greater than at least 0.75, greater than at least 0.1, greater than at least 0.15, greater than at least 0.2, or even greater than at least 0.25. In further embodiments, the outer coating 10 can have a dry coefficient of static friction, as measured against the umbilical line 100 at room temperature, of no greater than 1.25, such as, less than 1.15, less than 1.05, less than 1.0, less than 0.75, or even less than 0.5. Moreover, the outer coating 10 can comprise a material having a dry coefficient of static friction, as measured against the umbilical line 100 at room temperature, within a range between and including any of the values described above, such as, for example, between 0.6 and 1.1.

In certain, non-limiting embodiments, it may be desirable for the outer coating 10 to have a coefficient of static friction that is greater than 1.0 in order to better grip and secure the umbilical line and prevent sliding thereof within the passageway.

Figure 8:
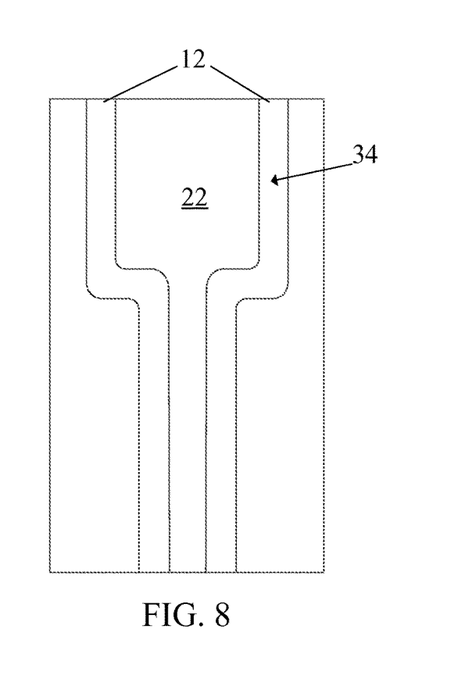
FIG. 8 includes a front view of a receiving member in accordance with an embodiment.

As contemplated herein, the receiving member 2 can comprise any number of passageways 12, however, a preferred embodiment includes two passageways, each adapted to receive and secure one umbilical line. When viewed from a front surface 22 of the receiving member 2, each passageway 12 can include at least one bend, such as, for example, a single right angle bend (FIGS. 1-6 and 9) or an S-shape bend (FIGS. 7 and 8). Each passageway 12 can alternatively include an acute-angled bend or an obtuse-angled bend. Moreover, each passageway 12 may have more than one bend disposed along a length thereof. These additional bends may provide enhanced gripping properties of the umbilical lines 100, and may further prevent the umbilical lines 100 from decoupling from the receiving member 2.

Figure 9:
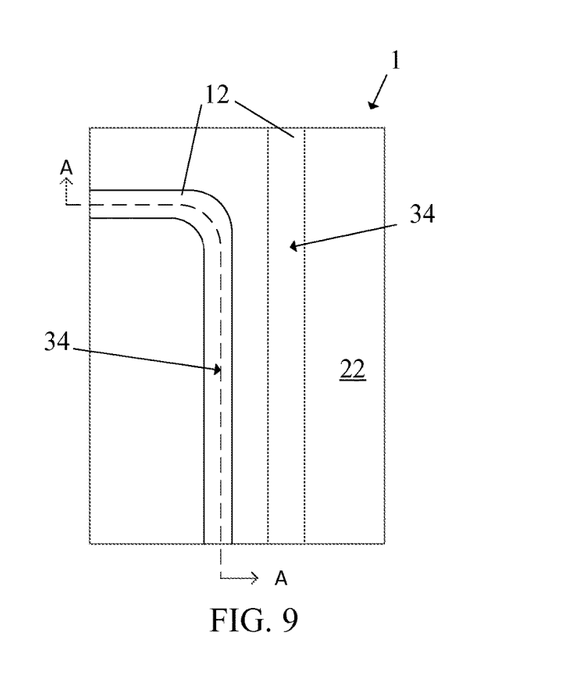
FIG. 9 includes a front view of a receiving member in accordance with an embodiment.

In particular embodiments, the passageways 12 can extend in a generally parallel direction (FIG. 11 to FIG. 13C). In other embodiments, the passageways 12 can extend at least partially in opposite directions (e.g., FIG. 3). Moreover, the passageways 12 can have different profiles when viewed from the first surface 22. For example, as illustrated in FIG. 9, one passageway can extend along a generally straight line while another passageway includes a bend. Passageways extending in different directions may be particularly important in scenarios where one umbilical line must be routed in a direction different from the other umbilical line.

In a particular embodiment, as illustrated in FIGS. 14 to 17B, the passageway may comprise one or more dimples 26 recessed into the body 8 of the receiving member 2. Each dimple 12 can be shaped to receive and securely hold an umbilical line therein. The dimples 26 can extend into the body 8 from the first surface 22 so as to not fully extend through the body 8. As illustrated in FIGS. 16A and 16B, the dimple 26 can comprise a rounded bottom profile (FIG. 16A) or a generally flat bottom profile (FIG. 16B). Moreover, in other embodiments (FIGS. 17A and 17B), the dimple 26 can include a polygonal shape when viewed in cross section.

In particular embodiments, the dimple 26 can include a coating to further increase the gripping properties and better secure the umbilical line 100. The coating can include any material that enhances gripping characteristics of the umbilical line-securing device 1, such as, for example, a polymer, such as an elastomer. An optional latching mechanism (not shown) can be installed on the body 8 of the receiving member 2 to secure the umbilical line 100 within the dimple 26. The latching mechanism (not shown) can include, for example, at least one of a latch, a lip, a projection extending into the dimple (e.g., FIGS. 17A and 17B), or any combination thereof.

Figure 17A:
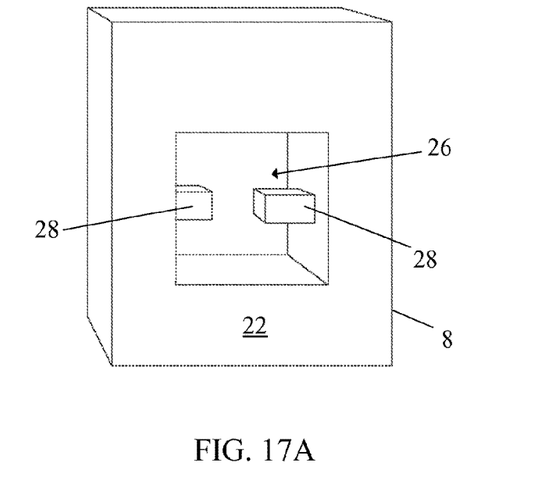
FIG. 17A includes a perspective view of a receiving member in accordance with an embodiment.
Figure 17B:
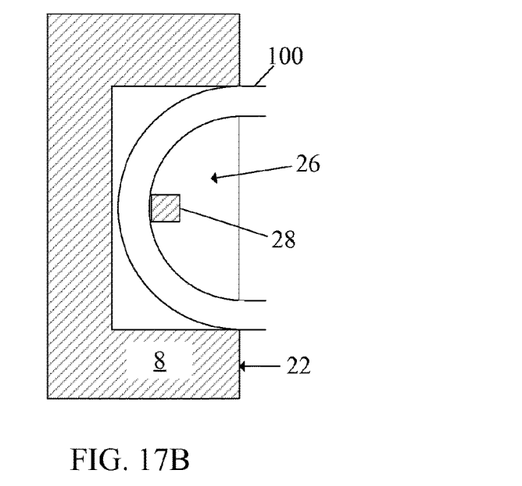
FIG. 17B includes a side view of a receiving member in accordance with an embodiment.

As illustrated in FIGS. 17A and 17B, the dimple 26 can include at least one feature 28 extending into the dimple 26. The feature 28 can secure the umbilical line 100 within the dimple 26 by bending or wedging the umbilical line 100 within the dimple 26. The feature 28 can be cubic (as illustrated), cylindrical, or comprise any other polygonal or arcuate shape. Moreover, the feature 28 can have any one of a serration, a projection, a channel, a polymer coating, or any combination thereof.

In a particular embodiment, the umbilical line 100 can initially be pushed into the dimple 26 at a location adjacent to the feature 26. After being inserted into the dimple 26 to a location beyond the feature 26, the umbilical line 100 can be translated laterally to a position behind the feature 26 (illustrated in installed format in FIG. 17B). In such a manner, the feature 26 can bend the umbilical line 100 and prevent the umbilical line from dislodging from the dimple 26.

As illustrated in FIG. 17A, the dimple 26 can include two features 28. Each feature 28 can extend a sufficient distance to support a single umbilical line. Moreover, a gap formed between the axial ends of the two features 28 can have a diameter that is less than a diameter of the umbilical lines, thereby preventing the umbilical lines from freely dislodging from the dimple 26.

Figure 13A:
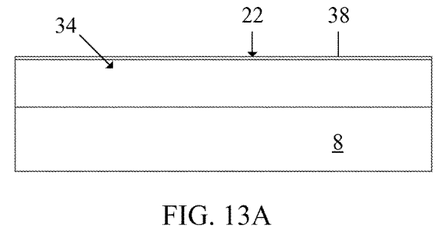
FIGS. 13A to 13C includes a cross-sectional side view of a receiving member in accordance with particular embodiments, as seen along Line C-C in FIG. 11.
Figure 13B:
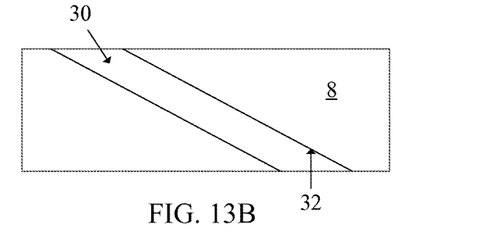
Figure 13C:
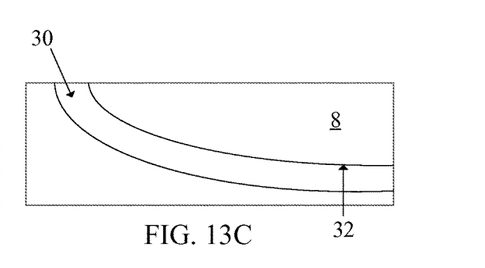
Figure 14:
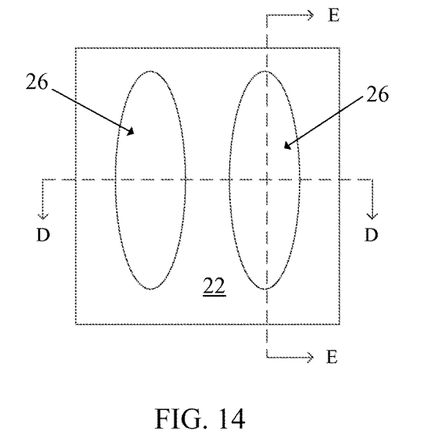
FIG. 14 includes a front view of a receiving member in accordance with an embodiment.
Figure 15:
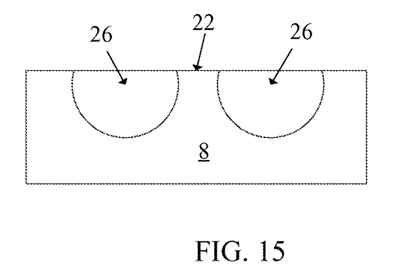
FIG. 15 includes a cross-sectional top view in accordance with an embodiment, as seen along Line D-D in FIG. 14.
Figure 16A:
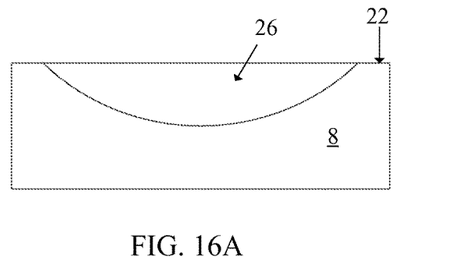
FIGS. 16A and 16B include cross-sectional side views of a receiving member in accordance with an embodiment, as seen along Line E-E in FIG. 14.
Figure 16B:
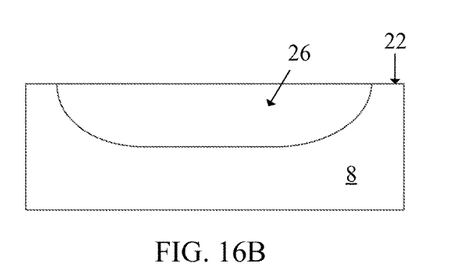
Figure 18:
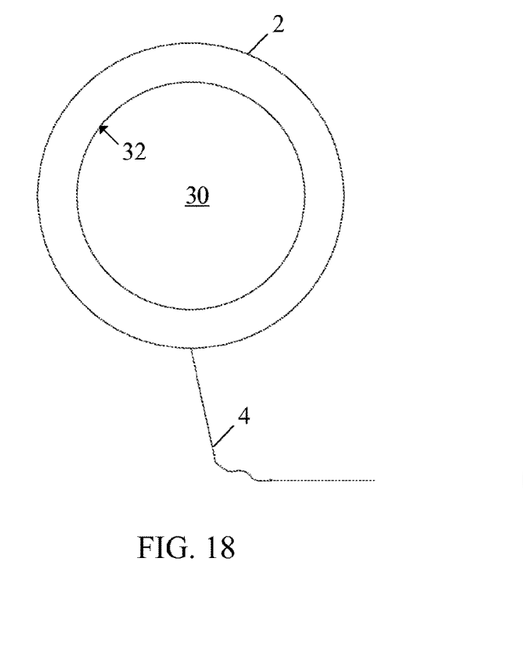
FIG. 18 includes a front view of a receiving member in accordance with an embodiment.

In another embodiment, illustrated in FIGS. 13B, 13C, and 18, the passageway may comprise an aperture 30 extending between two faces of the receiving member 2. In a first aspect, the aperture 30 may extend between two opposing faces of the receiving member 2 (FIG. 18). In another aspect, the aperture 30 may extend between two or more adjacent faces of the receiving member 2 (FIGS. 13B and 13C). As illustrated in FIG. 18, the aperture 30 can be shaped and sized to receive two umbilical lines. In this regard, the umbilical lines can be jointly inserted into a single aperture. Alternatively, as illustrated in FIGS. 13B and 13C, each aperture 30 can be shaped and sized to receive a single umbilical line. In this regard, two apertures 30 can be disposed within the receiving member 2, and each aperture can receive and support one umbilical line. In further embodiments, an inner surface 32 formed by the aperture 30 can include a coating to increase the gripping properties and better secure the umbilical line 100.

Figure 6:
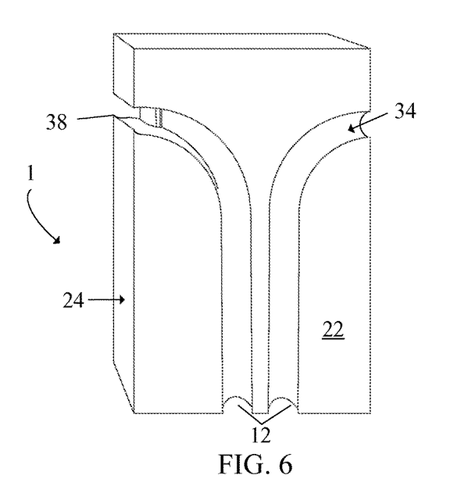
FIG. 6 includes a perspective view of a receiving member in accordance with an embodiment.

In certain embodiments, such as illustrated in FIGS. 1 to 13A, the passageway may comprise a channel 34 disposed on a first surface 22 of the receiving member 2. In a further embodiment, as illustrated in FIG. 6, the channel 34 may span several surfaces of the receiving member 2, e.g., the first surface 22 and a second surface 24. In such a manner, a length of the channel 34 may extend in at least two geometric planes. This may provide the channel 34 with additional gripping capabilities and may reduce the likelihood that the umbilical line dislodges therefrom.

When viewed in a direction along a length of the channel 34 (FIGS. 4, 10, and 12-13C), the channel 34 may comprise a polygonal cross-sectional shape, a circular cross sectional shape, or any combination thereof. In a particular embodiment, the channel 34 can have a cross sectional area, $A_C$, as measured by the cross-sectional area of the channel 34, as extending from the first surface 22 of the receiving member 2 into the body 8. The umbilical line 100 intended to be secured within the channel 34 can have a cross sectional area, $A_{UL}$, as measured by the average cross-sectional area of the umbilical line 100. In certain embodiments $A_C$ can be at least 0.8 $A_{UL}$, such as at least 0.9 $A_{UL}$, at least 1.0 $A_{UL}$, at least 1.1 $A_{UL}$, or at least 1.2 $A_{UL}$. In further embodiments, $A_C$ can be no greater than 2.0 $A_{UL}$, such as no greater than 1.8 $A_{UL}$, no greater than 1.6 $A_{UL}$, no greater than 1.4 $A_{UL}$, or no greater than 1.25 $A_{UL}$. Moreover, the ratio of $A_C$ to $A_{UL}$ can be within a range of between and including any of the values described above, such as, for example, between 0.95 and 1.05.

A person of ordinary skill in the art will understand that there may be more than one size umbilical line, e.g., 3.5F and 5F. As contemplated herein, the passageways 12 on a single umbilical line-securing device can have different sizes to accommodate the different sized umbilical lines. For example, an umbilical line-securing device can have a passageway adapted to receive and secure a 3.5F umbilical line while another passageway is adapted to receive and secure a 5F umbilical line. For example, in particular embodiments, the umbilical line-securing device can include four passageways—two passageways can be sized to receive a 3.5F umbilical line and two passageways can be sized to receive a 5F umbilical line. In this regard, a single umbilical line-securing device can secure any number of varying umbilical lines in varying configurations. It may also be advantageous to include several passageways in several orientations and configurations such that proper routing of the umbilical lines can be achieved as necessary. Indicia can indicate to a user, e.g., a nurse, the appropriate passageway for each of the same—or differently-sized umbilical lines. Moreover, in the event other size umbilical lines become used, the relative size of the passageways 12 can be adjusted to accommodate these new sized umbilical lines.

Figure 5:
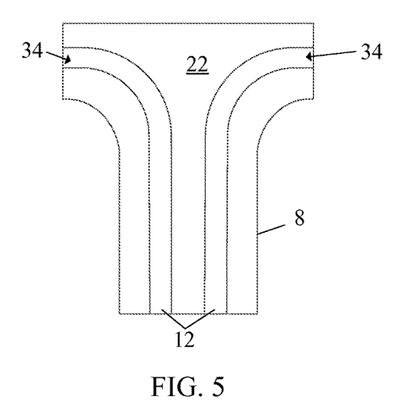
FIG. 5 includes a front view of a receiving member in accordance with an embodiment.

In certain embodiments, the umbilical line-securing device 1 can include two channels 34 and 34. The two channels 34 and 34 can extend along the same or different surfaces of the receiving member 2 and can be shaped and oriented in similar or different configurations. In particular embodiments, the two channels 34 and 34 can form a T-shape along a face of the receiving member 2 (FIG. 5). In this regard, both channels 34 and 34 can have first ends on the same face of the receiving member 2 and second ends can extend to opposite faces of the receiving member 2. In further embodiments (not illustrated), the two channels can form a Y-shape along a face of the receiving member. In this regard, both channels can have first ends on the same surface of the receiving member and second ends can extend to opposite faces of the receiving member. Alternatively, the channels 34 and 34 can form any other shape along the receiving member 2.

In certain embodiments, the receiving member can further include one or more gripping members (not illustrated) extending from the body into the channel. The gripping members may include small tines, teeth, ridges, bumps, or other similar projections adapted to form an interference fit with, or slightly pierce, walls of the umbilical lines. In this regard, the gripping members can further enhance grip with the umbilical line and prevent axial translation of the umbilical line within the channel.

Figure 10:
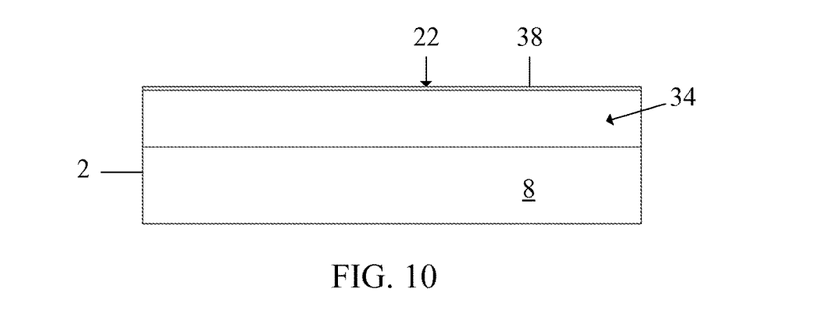
FIG. 10 includes a cross-sectional side view of a receiving member in accordance with an embodiment, as seen along Line A-A in FIG. 9.
Figure 11:
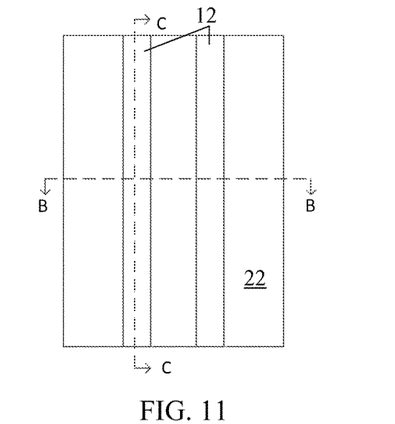
FIG. 11 includes a front view of a receiving member in accordance with an embodiment.
Figure 12:
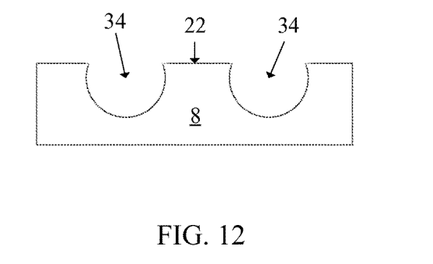
FIG. 12 includes a cross-sectional top view of a receiving member in accordance with an embodiment, as seen along Line B-B in FIG. 11.

In particular embodiments, such as illustrated in FIG. 10, the receiving member 2 can further include a lip 38 partially extending over the channel 34 along at least a portion of a length of the channel 34. The lip 38 can have a diameter, as measured by a shortest distance from the innermost edge of the lip 38 to the opposite side of the channel 34 along the first surface 22 of the body 8, that is smaller than the maximum diameter of the channel 34. In such a manner, the umbilical line can compress during insertion into the'channel 34, when passing the lip 38, and can return to its previous diameter after entering the channel 34. In this regard, the lip 38 can prevent the umbilical line from decoupling from within the channel 34. In further embodiments, the receiving member 2 can include two lips 38 disposed along opposite sides of the channel 34.

Referring again to FIG. 6, the lip 38 may extend along a portion of the channel 34. In this regard, the lip 38 can act as a strain reliever and allow easier securement of the umbilical line within the channel 34. Alternatively, as illustrated in FIG. 10, the lip 38 can extend along the full length of the channel 34.

Figure 19:
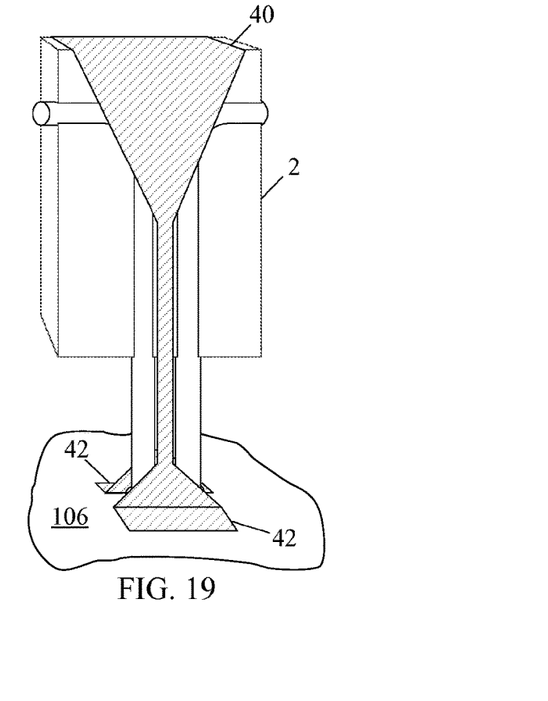
FIG. 19 includes a perspective view of an umbilical line-securing device in accordance with an embodiment.

In the days following birth, the umbilical stump can often dry and fall off, leaving behind an umbilicus into which the umbilical lines can remain. As a result, the umbilical line-securing device can become disconnected from the baby. As illustrated in FIG. 19, a modified securing member 40 can be attached to the receiving member 2 and can secure the receiving member 2 to the baby 106, e.g., by tabs 42. In certain embodiments, the tabs 42 can include an adhesive or a bonding agent. A person of ordinary skill in the art will recognize that many of the problems associated with the attachment of adhesive to the skin of a newborn baby, e.g., fragility and vulnerability to infection, dissipate in the days following birth. Therefore, an adhesive can be more safely applied to the baby's kin in the days and weeks following birth.

Items.

Item 1. An umbilical line-securing device comprising a receiving member adapted to receive at least one umbilical line, wherein the receiving member is adapted to be disposed at a location proximate to an umbilical stump.

Item 2. An umbilical line-securing device comprising a receiving member adapted to receive and secure at least one umbilical line, wherein the receiving member is adapted to be secured to an umbilical stump.

Item 3. An umbilical line-securing device comprising: a receiving member adapted to receive and secure at least one umbilical line; and a securing member adapted to secure the receiving member at a location adjacent to an umbilical stump.

Item 4. An umbilical line-securing device comprising: a receiving member comprising: a body; a passageway adapted to receive an umbilical line; and a fastening element adapted to secure the umbilical line within the passageway; and a securing member engaged with the receiving member, the securing member adapted to secure the receiving member to an umbilical stump.

Item 5. An umbilical line-securing device adapted to secure at least one umbilical line to an umbilical stump, wherein the umbilical securing device is secured to the umbilical stump without the use of an adhesive.

Item 6. An umbilical line-securing device adapted to secure at least one umbilical line to an umbilical stump, wherein the at least one umbilical line is secured to the umbilical securing device without the use of an adhesive.

Item 7. The umbilical line-securing device according to any one of the preceding items, wherein the receiving member comprises a body.

Item 8. The umbilical line-securing device according to any one of the preceding items, wherein the receiving member is generally polygonal.

Item 9. The umbilical line-securing device according to any one of the preceding items, wherein the receiving member has a maximum height, $H_{RM}$, a maximum width, $W_{RM}$, and maximum thickness, $T_{RM}$, wherein $H_{RM}$ is greater than $W_{RM}$, and wherein $W_{RM}$ is greater than $T_{RM}$.

Item 10. The umbilical line-securing device according to any one of the preceding items, wherein the receiving member is monolithic.

Item 11. The umbilical line-securing device according to any one of items 1-9, wherein the receiving member comprises at least two components, such as at least three components, at least four components, at least five components, at least six components, at least seven components, at least eight components, at least nine components, or at least ten components.

Item 12. The umbilical line-securing device according to item 11, wherein the at least two components are connected together.

Item 13. The umbilical line-securing device according to any one of items 11 or 12, wherein the at least two components are statically affixed together.

Item 14. The umbilical line-securing device according to any one of items 11 or 12, wherein the at least two components are attached by at least one hinge.

Item 15. The umbilical line-securing device according to any one of items 11, 12, or 14, wherein the at least two components are moveable relative to each other.

Item 16. The umbilical line-securing device according to any one of items 1-4, wherein, when viewed from a front view, the receiving member comprises a generally Y-shape.

Item 17. The umbilical line-securing device according to any one of items 1-4 or 16, wherein when viewed from a front view, the receiving member comprises a generally T-shape.

Item 18. The umbilical line-securing device according to any one of the preceding items, wherein the receiving member is at least partially formed by injection molding.

Item 19. The umbilical line-securing device according to any one of the preceding items, wherein the receiving member is formed by injection molding.

Item 20. The umbilical line-securing device according to any one of the preceding items, wherein the receiving member is at least partially formed by extruding.

Item 21. The umbilical line-securing device according to any one of the preceding items, wherein the receiving member is at least partially formed by casting.

Item 22. The umbilical line-securing device according to any one of the preceding items, wherein the receiving member at least partially comprises a polymer.

Item 23. The umbilical line-securing device according to any one of the preceding items, wherein the receiving member at least partially comprises a metal.

Item 24. The umbilical line-securing device according to any one of the preceding items, wherein the receiving member further comprises an outer coating.

Item 25. The umbilical line-securing device according to item 24, wherein the outer coating at least partially comprises a polymer.

Item 26. The umbilical line-securing device according to any one of items 24 or 25, wherein the outer coating at least partially comprises an elastomer.

Item 27. The umbilical line-securing device according to any one of items 24-26, wherein the outer coating at least partially comprises silicone.

Item 28. The umbilical line-securing device according to any one of items 24-27, wherein the outer coating at least partially comprises rubber.

Item 29. The umbilical line-securing device according to any one of items 24-28, wherein the outer coating has a thickness of between 0.005 inches and 0.50 inches.

Item 30. The umbilical line-securing device according to any one of items 24-29, wherein the outer coating has a thickness of between 0.05 inches and 0.25 inches.

Item 31. The umbilical line-securing device according to any one of items 24-30, wherein the outer coating has a thickness of between 0.05 inches and 0.15 inches.

Item 32. The umbilical line-securing device according to any one of items 24-31, wherein the receiver further comprises an intermediate layer disposed between the receiving member and the outer coating.

Item 33. The umbilical line-securing device according to item 32, wherein the intermediate member comprises an adhesion promoting layer.

Item 34. The umbilical line-securing device according to any one of items 24-33, wherein the outer coating comprises a material having a static coefficient of friction, as measured against the umbilical line, that is greater than at least 0.01, greater than at least 0.05, greater than at least 0.75, greater than at least 0.1, greater than at least 0.15, greater than at least 0.2, or greater than at least 0.25.

Item 35. The umbilical line-securing device according to any one of the preceding items, wherein the receiving member further comprises a passageway adapted to receive the at least one umbilical line.

Item 36. The umbilical line-securing device according to item 35, wherein the passageway comprises a dimple extending at least partially into the receiving member.

Item 37. The umbilical line-securing device according to item 35, wherein the passageway comprises an aperture extending through the receiving member.

Item 38. The umbilical line-securing device according to item 35, wherein the passageway comprises a channel.

Item 39. The umbilical line-securing device according to item 38, wherein the channel is disposed on a first surface of the receiving member.

Item 40. The umbilical line-securing device according to any one of items 38 or 39, wherein the channel is disposed on at least two surfaces of the receiving member.

Item 41. The umbilical line-securing device according to any one of items 38-40, wherein, when viewed in cross section, the channel comprises a generally polygonal cross sectional profile.

Item 42. The umbilical line-securing device according to any one of items 38-40, wherein, when viewed in cross section, the channel comprises a generally circular cross sectional profile.

Item 43. The umbilical line-securing device according to any one of items 38-42, wherein the channel comprises a cross sectional area, $A_C$, as measured by the cross-sectional area of the channel extending from the face of the receiving member, wherein the channel is adapted to receive an umbilical line having a cross sectional area, $A_{UL}$, and wherein $A_C$ is at least 0.8 $A_{UL}$, such as at least 0.9 $A_{UL}$, at least 1.0 $A_{UL}$, at least 1.1 $A_{UL}$, or at least 1.2 $A_{UL}$.

Item 44. The umbilical line-securing device according to item 43, wherein $A_C$ is no greater than 2.0 $A_{UL}$, such as no greater than 1.8 $A_{UL}$, no greater than 1.6 $A_{UL}$, no greater than 1.4 $A_{UL}$, or no greater than 1.25 $A_{UL}$.

Item 45. The umbilical line-securing device according to any one of items 38-44, wherein the channel extends between a first edge of the receiving member and a second edge of the receiving member, and wherein the first and the second edges are on opposite sides of the receiving member.

Item 46. The umbilical line-securing device according to any one of items 38-44, wherein the channel extends between a first edge of the receiving member and a third edge of the receiving member, and wherein the first and the third edges are on adjacent sides of the receiving member.

Item 47. The umbilical line-securing device according to any one of items 38-46, wherein the channel comprises a central line, and wherein a segment of the central line of the channel lies along a straight line.

Item 48. The umbilical line-securing device according to any one of items 38-46, wherein a central line of the channel lies along a straight line.

Item 49. The umbilical line-securing device according to any one of items 38-46, wherein a central line of the channel comprises an S-shape.

Item 50. The umbilical line-securing device according to any one of items 38-46, wherein a central line of the channel comprises a right angle bend.

Item 51. The umbilical line-securing device according to item 50, wherein the right angle bend comprises a gradual bend.

Item 52. The umbilical line-securing device according to any one of items 38-51, wherein the channel further comprises a lip.

Item 53. The umbilical line-securing device according to item 52, wherein, when viewed along a plane perpendicular to the channel, the lip is contiguous with a surface of the receiving member and extends over the channel.

Item 54. The umbilical line-securing device according to any one of items 52 or 53, wherein the maximum width of the channel, as measured in a direction perpendicular to the channel, is greater than the width of the channel, as measured along the surface of the receiving member.

Item 55. The umbilical line-securing device according to any one of items 52-54, wherein the channel has an opening width, as measured in a plane perpendicular to the surface, that is less than the diameter of the umbilical line.

Item 56. The umbilical line-securing device according to any one of the preceding items, wherein the umbilical securing device comprises two passageways, each passageway adapted to receive an umbilical line.

Item 57. The umbilical line-securing device according to any one of items 1, 2, or 5-56, wherein the umbilical line-securing device further comprises a securing member.

Item 58. The umbilical line-securing device according to any one of items 3, 4, or 57, wherein the securing member is connected to the receiving member, and wherein the securing member is adapted to engage an umbilical stump.

Item 59. The umbilical line-securing device according to any one of items 3, 4, 57, or 58, wherein the securing member is directly connected to the receiving member.

Item 60. The umbilical line-securing device according to any one of items 3, 4, 57, or 58, wherein the securing member is indirectly connected to the receiving member.

Item 61. The umbilical line-securing device according to any one of items 3, 4, or 57-60, wherein the securing member comprises a thread.

Item 62. The umbilical line-securing device according to any one of items 3, 4, or 57-61, wherein the securing member comprises a suture.

Item 63. The umbilical line-securing device according to any one of items 3, 4, or 57-62, wherein the securing member comprises a length of at least 0.5 inches, at least 1 inch, at least 2 inches, at least 3 inches, at least 4 inches, or at least 5 inches.

Item 64. The umbilical line-securing device according to item 63, wherein the length is no greater than 25 inches, no greater than 20 inches, no greater than 15 inches, no greater than 10 inches, or no greater than 6 inches.

Item 65. The umbilical line-securing device according to any one of items 3, 4, or 57-64, wherein the umbilical line-securing device further comprises a fastening element connected to the securing member.

Item 66. The umbilical line-securing device according to item 65, wherein the fastening element is nonadhesive.

Item 67. The umbilical line-securing device according to item 65, wherein the fastening element comprises a needle.

Item 68. The umbilical line-securing device according to item 67, wherein the needle is curved.

Item 69. An adhesiveless umbilical line-securing device adapted to secure an umbilical line at a location adjacent to an umbilical stump.

Item 70. The umbilical line-securing device according to any one of the preceding items, wherein the umbilical line-securing device has a mass of less than 500 grams, less than 250 grams, less than 100 grams, less than 75 grams, less than 50 grams, less than 25 grams, or less than 10 grams.

Item 71. The umbilical line-securing device according to any one of the preceding items, wherein the umbilical line-securing device has a mass of at least 0.1 grams, at least 0.5 grams, at least 1 gram, or at least 5 grams.

Item 72. A method of securing an umbilical line, comprising: providing the device according to any one of the preceding items; attaching an umbilical line to the device; and securing the device to an umbilical stump.

Item 73. A method of securing an umbilical line, comprising: providing the device according to any one of items 1-69; securing the device to an umbilical stump; and attaching an umbilical line to the device.

Item 74. A method of securing an umbilical line, comprising: providing an adhesiveless receiving member adapted to receive at least one umbilical line; engaging the umbilical line with the receiving member; and nonadhesively securing the receiving member at a location proximate to an umbilical stump.

Item 75. A method of securing an umbilical line, comprising: providing an adhesiveless receiving member adapted to receive at least one umbilical line; nonadhesively securing the receiving member at a location proximate to an umbilical stump; and engaging the umbilical line with the receiving member.

The embodiments presented herein may permit a user, e.g., a nurse, to more easily and quickly secure or readjust umbilical lines with respect to an umbilical stump. Specifically, because the umbilical line-securing device is adhesiveless, a user can quickly detach the umbilical lines from the umbilical line-securing device, reposition the umbilical lines, and reinsert the umbilical lines into the umbilical line-securing device. This can be particularly advantageous during initial attachment and securement of the umbilical lines, as a user is often required to adjust the umbilical lines within the baby to ensure proper positioning. Moreover, because the skin of a baby is sensitive and subject to infection, particularly immediately following birth, it may be advantageous to secure the umbilical line to the baby without the use of an adhesive.

The embodiments provide a combination of features, which can be combined in various manners to describe and define a method and system of the embodiments. The description is not intended to set forth a hierarchy of features, but different features that can be combined in one or more manners to define the invention. In the foregoing, reference to specific embodiments and the connection of certain components is illustrative. It will be appreciated that reference to components as being coupled or connected is intended to disclose either direct connection between said components or indirect connection through one or more intervening components as will be appreciated to carry out the methods as discussed herein.

As such, the above-disclosed subject matter is to be considered illustrative, and not restrictive, and the appended claims are intended to cover all such modifications, enhancements, and other embodiments, which fall within the true scope of the present invention. Thus, to the maximum extent allowed by law, the scope of the present invention is to be determined by the broadest permissible interpretation of the following claims and their equivalents, and shall not be restricted or limited by the foregoing detailed description.

The disclosure is submitted with the understanding that it will not be used to interpret or limit the scope or meaning of the claims. In addition, in the foregoing disclosure, various features may be grouped together or described in a single embodiment for the purpose of streamlining the disclosure. This disclosure is not to be interpreted as reflecting an intention that the embodiments herein limit the features provided in the claims, and moreover, any of the features described herein can be combined together to describe the inventive subject matter. Still, inventive subject matter may be directed to less than all features of any of the disclosed embodiments.

The invention claimed is:

1. An umbilical line-securing device comprising:
    a receiving member comprising:
        a body defining a first passageway recessed from a surface of the body, wherein the first passageway is adapted to receive a first umbilical line; and
        a plurality of posts extending outward from the surface of the body in a direction normal to the surface of the body, wherein the plurality of posts comprise a first post and a second post, wherein the first and second posts are disposed on opposite sides of the first passageway, wherein the first and second posts are cylindrical, and wherein an area between the first and second posts is adapted to receive the first umbilical line as it enters the first passageway;
    a second component selectively moveable with respect to the receiving member, wherein the receiving member and second component are selectively closable, wherein, when closed, the umbilical line-securing device is adapted to contact the first umbilical line at the first passageway, the first post, the second post, and the second component along a line extending around the first umbilical line in a direction perpendicular to a length of the first passageway, and wherein, in the closed configuration, the first and second posts extend into the second component; and
    an attachment device adapted to receive a securing device adapted to nonadhesively secure the umbilical line-securing device to an umbilical stump.

2. The umbilical line-securing device of claim 1, further comprising a second passageway recessed from the surface of the body, wherein the second passageway is adapted to receive a second umbilical line, and wherein a second plurality of posts extends from the surface of the body and is adapted to guide the second umbilical line into the second passageway.

3. The umbilical line-securing device according to claim 2, wherein the second plurality of posts comprises:
    a third post extending from the body at a location immediately adjacent to the second passageway; and
    a fourth post extending from the body at a location immediately adjacent to the second passageway,
    wherein the thrid and fourth posts are disposed on opposite sides of the second passageway, and wherein the third and fourth posts extend from the body in a direction normal to the surface.

4. The umbilical line-securing device according to claim 3, wherein the third and fourth posts are generally cylindrical, and wherein the third and fourth posts are generally parallel with respect to one another.

5. The umbilical line-securing device according to claim 2, wherein the first and second passageways are spaced apart from one another, and wherein an entire length of at least one of the first and second passageways lies along a straight line.

6. The umbilical line-securing device according to claim 2, wherein the attachment device comprises a loop adapted to engage a suture adapted to secure the umbilical line-securing device to a patient.

7. The umbilical line-securing device according to claim 2, wherein the first passageway has a different diameter than the second passageway, and wherein the second passageway extends the entire distance between opposite edges of the body.

8. The umbilical line-securing device according to claim 7, wherein the first passageway includes a straight portion and a bent portion, and wherein the umbilical line-securing device is adapted to receive the first umbilical line at least partially below the surface of of the body in both the straight and bent portions of the first passageway.

9. The umbilical line-securing device according to claim 1, wherein the plurality of posts further comprises a third post and a fourth post extending from the surface of the body, wherein the first and second posts are disposed on a first longitudinial half of the first passageway, and wherein the third and fourth posts are disposed on a second longitudinal half of the first passageway.

10. The umbilical line-securing device according to claim 9, wherein the first, second, third, and fourth posts all have a same shape and a same size.

11. The umbilical line-securing device according to claim 1, wherein the first passageway has a generally semi-circular cross-sectional profile as viewed along the entire length of the first passageway.

12. The umbilical line-securing device according to claim 1, wherein the first and second posts have a uniform cross section.

13. The umbilical line-securing device according to claim 1, wherein the second component has an inner surface adapted to receive the plurality of posts when the umbilical line-securing device is closed.

14. The umbilical line-securing device according to claim 1, wherein the surface extends between first and second edges of the body, wherein the first and second edges are generally opposite one another, wherein the first passageway extends continuously along the surface an entire distance between the first and second edges, and wherein the first passageway is adapted to contact the first umbilical line along an entire length of the first passageway.

15. The umbilical line-securing device according to claim 1, wherein the plurality of posts are monolithic with the body.

16. The umbilical line-securing device according to claim 1, wherein the receiving member and second component are adapted to contact the first umbilical line along an entire length of the first passageway, and wherein a contact interface between the first umbilical line, receiving member, and second component is continuous along the entire length of the first passageway.

17. The umbilical line-securing device of claim 1, wherein the first passageway has a uniform cross-sectional profile as measured along an entire length of the first passageway.

18. The umbilical line-securing device according to claim 1, wherein the receiving member further comprises an outer coating.

19. The umbilical line-securing device according to claim 1, wherein the first post comprises a plurality of first posts disposed on a first lateral side of the first passageway and the second post comprises a plurality of second posts disposed on a second lateral side of the first passageway, wherein the first and second lateral sides of the first passageway are opposite one another, and wherein the plurality of first and second posts are adapted to contact the first umbilical line when the umbilical line-securing device is closed.

20. The umbilical line-securing device according to claim 1, wherein the umbilical line-securing device is adapted to releasably secure the first umbilical line permitting relocation of the first umbilical line with respect to the umbilical stump.

* * * * *